(12) United States Patent
Royer (10) Patent No.: US 6,326,142 B1
(45) Date of Patent: *Dec. 4, 2001

(54) QUANTITATIVE DETECTION OF MACROMOLECULES WITH FLUORESCENT OLIGONUCLEOTIDES

(75) Inventor: Catherine A. Royer, Madison, WI (US)

(73) Assignee: PanVera Corporated, Madison, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/030,872

(22) Filed: Feb. 18, 1998

Related U.S. Application Data

(63) Continuation of application No. 08/516,331, filed on Aug. 17, 1995, now Pat. No. 5,756,292, which is a continuation of application No. 07/980,283, filed on Nov. 23, 1992, now Pat. No. 5,445,935.

(51) Int. Cl.[7] .................................................. C12Q 1/68
(52) U.S. Cl. .............................. 435/6; 530/350; 536/26.6
(58) Field of Search ..................... 435/6, 7.1; 536/26.6; 530/350

(56) References Cited

PUBLICATIONS

Matthews, Analytical Biochemistry 19, 1–25 (1988).*
Heyduk et al., Proc Natl Acad Sci, 87:1744–48, Mar. 1990.*

* cited by examiner

Primary Examiner—Scott W. Houtteman
(74) Attorney, Agent, or Firm—Shelby J. Walker, Esq.; Andrew S. Marks, Esq.

(57) ABSTRACT

A method is described by which the association between an oligonucleotide labeled by attachment of a fluorophore and another macromolecule such as a protein or nucleic acid may be determined quantitatively in solution accurately and with high sensitivity. In the performance of this method the polarization of fluorescence of an extrinsic fluorescence probe that is covalently coupled to the oligonucleotide is determined. Changes in fluorescence polarization are related directly to the degree of association between the labeled oligonucleotide and another macromolecule and may be used to quantify the association. Because of its high sensitivity and accuracy, this method may be used to make reliable quantitative measurements of very small amounts of complexes formed between labeled oligonucleotides and proteins, nucleic acids or other macromolecules. The method also allows the accurate calculation of important biochemical parameters such as dissociation constants. The method, which is rapid and solution-based, has a broad range of applications in biochemistry, genetic cloning and molecular biology, as well as in clinical diagnostics.

8 Claims, 8 Drawing Sheets

QUANTITATIVE DETECTION OF MACROMOLECULES WITH FLUORESCENT OLIGONUCLEOTIDES

This application is a continuation of application Ser. No. 08/516,331, filed on Aug. 17, 1995, now U.S. Pat. No. 5,756,292 which is a Continuation of application Ser. No. 07/980,283 filed Nov. 23, 1992, now U.S. Pat. No. 5,445,935 the entire contents of which are hereby incorporated by reference.

BACKGROUND OF THE INVENTION

1. Field of the Invention

The invention relates to the use of measurement of the polarization of the fluorescence emission from a labelled macromolecule in order to assess the binding of the labelled macromolecule to a second macromolecule. Thus, the invention is directed to analytic methods for determining such binding in a quantitative fashion. The invention is also directed to apparatus for conducting binding analyses using measurement of fluorescence polarization.

2. Description of the Related Art

The use of labeled oligonucleotides as probes in macromolecular analysis is an important technique in molecular biology. Oligonucleotides have been labeled with radioisotopes, enzymes or fluorescent molecules. Because of the relatively low molecular weights of oligonucleotides, and the common availability of instrumentation for their automated synthesis, oligonucleotides are often used in blot-hybridization procedures or in gel-retardation assays for the detection and qualitative evaluation of macromolecules with which they may associate. These macromolecules may be either proteins, RNA molecules or DNA molecules In a standard blot-hybridization procedure, the target macromolecule is separated bag electrophoresis in a gel matrix, commonly agarose or polyacrylamide. It is then transferred to a membrane in such a way as to preserve its relative spatial positioning within the gel matrix and fix it stably to the membrane. Alternatively, the macromolecule may be attached to the membrane without prior electrophoresis. The presence of the macromolecule on the membrane is determined by binding to it a labeled oligonucleotide and subjecting the complex to autoradiography or, if the oligonucleotide is labeled with radioisotope, by scintillation counting.

In a standard gel retardation assay an oligonucleotide that has been labelled with radioisotope or other detectable moiety is electrophoresed in a gel matrix, commonly made of agarose or acrylamide, under non-denaturing conditions. The labelled oligonucleotide is also associated with a protein that may bind to the oligonucleotide and the mixture is electrophoresed on a gel, commonly in a neighboring lane, for comparing with the unassociated oligonucleotide. Because of its higher molecular weight and less negative charge, the protein will exhibit lower mobility in the gel than the unassociated oligonucleotide If the oligonucleotide forms a stable complex with the protein, it will also exhibit a lower mobility than that of the unassociated oligonucleotide. Comparison of the mobility of the oligonucleotide mobility in the presence and absence of the protein allows qualitative determination of whether a complex forms between the two macromolecules. These basic methods are used for a very large variety of determinations in basic genetic research, genetic engineering, the medical sciences, and agricultural testing.

The present invention relates to a method for detecting and quantitating complexation between nucleic acids and proteins or other macromolecules which comprises the measurement of the polarization of fluorescence of an extrinsic fluorophore covalently coupled to an oligonucleotide. The oligonucleotide can be an oligodeoxyribonucleotide, an oligonribonucleotide or a co-polymer of both. The nucleotide bases can be derivatized, as can the backbone chain. The oligonucleotide can be single-, double- or triple-stranded. The length of the oligonucleotide is determined by the specific experiment being conducted, but is preferably less than 40 residues long, more preferably being less than 25 residues long and most preferably 8–10 residues long.

The fluorophore is incorporated into the oligonucleotide at any position using standard automated DNA synthesis techniques and fluorescently labeled amino-linker compounds (e.g. those available from Clontech, Inc., La Jolla, Calif.). Alternately, unlabeled amino-linker compounds can be incorporated and subsequently labeled with the fluorescent compound. A variety of fluorophores may be used, including fluorescein, eosin, coumarin and dansyl derivatives. The fast rotation about the short axis of the oligonucleotide results in a low value of the fluorescence polarization of the probe covalently coupled to the oligonucleotide. This value is obtained by exciting the fluorescently labeled oligonucleotide with the appropriate wavelength of plane polarized exciting light and monitoring the emission of light polarized in the planes parallel and perpendicular to the plane of polarization of the exciting light. The fluorescence polarization is calculated as:

$$p = (I_\parallel - I_L)/(I_\parallel + I_L)$$

where $I_\parallel$ is the intensity of the emitted light polarized in a plane parallel to the plane of polarization of the exciting light and $I_L$ is the intensity of the emitted light polarized in a plane perpendicular to the plane of polarization of the exciting light. The anisotropy of the emission is $$2/3[1/(1/p - 1/3)]$$

This value is analogous to the polarization yet linear with respect to the total fluorescence emission intensity.

Fluorescence polarization is the basis for a series of patented assays for the clinical detection of drugs, steroids and other antigens (U.S. Pat. Nos. 4,269,511; 4,516,856; 4,585,362; 4,668,640; 4,784,961 4,902,630; 4,952,691; 5,066,426; European patent application 86102035.2). Although there are a number of variations, change in the fluorescence polarization of fluorescein upon changing its interaction with specific or non-specific antibodies when the drug of interest is present in the assay solution. If the presence of the drug results in the dissociation of the fluorescein-antibody complex, for example, then the fluorescence polarization will exhibit a large decrease. The sensitivity of these assays is less than 10 pM. Urios and Cittanova (15) describe the use of fluorescently labeled Fab fragments of antibodies to perform fluorescence polarization measurements. The sensitivity of their assay is 2.5 $\mu$M. The use of a fluorescent-labeled oligonucleotide probe was reported by Murakami et al (17). Their reported sensitivity was 100 nanomolar. Giedroc et al. (16) used fluorescence anisotropy in evaluating the presence of single stranded DNA molecules. Their assays were conducted at oligonucleotide concentrations of 2 to 8 $\mu$M.

SUMMARY OF THE INVENTION

One object of the present invention is to provide a method by which the binding of two macromolecules to each other can be detected in the solution phase by measuring the polarization of the fluorescent emission from a probe moiety. Preferably, the probe is attached to one macromolecule and binding is determined directly by an increase in the fluorescence polarization. A second object of the present invention is to provide an apparatus suitable for performing fluorescence polarization measurements with very high sensitivity so as to be able to perform such measurements quantitatively on very small samples. In preferred embodiments of the apparatus, detection of the polarization of the fluorescent emission of as little as one femtomole of fluorophore can be detected.

A third object of the present invention is to provide diagnostic methods which are based upon measuring the binding of a polynucleotide to a second polynucleotide, or alternatively to a protein, by means of quantitation of the polarization of the emission from a fluorophore covalently attached to either said polynucleotide.

DETAILED DESCRIPTION OF THE INVENTION

The present invention defines methods by which the association between a fluorescently labeled oligonucleotide and another macromolecule such as a protein or a nucleic acid may be measured rapidly, accurately and with high sensitivity in solution. In particular, this invention relates to the detection of complex formation (i.e., formation of a stable, specific noncovalent association) between the oliqonucleotide and the target macromolecule, each at very low concentration, through the measurement of the polarization of fluorescence of an extrinsic fluorescent probe covalently coupled to the oligonucleotide. The fluorescence polarization detection is based upon the increase in the rotational correlation time of the probe covalently linked to the oligonucleotide as a result of the increase in the size of the tumbling particle when the protein or other macromolecule is complexed with it, compared to the rotational correlation time of the fluorescently labeled oligonucleotide in the absence of interacting macromolecules. Using the appropriate instrumentation, measurements of fluorescence polarization may be made very rapidly, usually on the order or 5–10 minutes. In contrast, a blot-hybridization or gel retardation analysis, as described above, will take a full day—and very often longer—to complete. Alternative uses of fluorescence polarization measurements in macromolecular analysis have been described (15–17). However, these methods do not provide adequate sensitivity to make them useful in practical applications. Biological macromolecules are often found in extremely small amounts, requiring analytical sensitivities at less than nanomolar levels. The method described in the present invention allows measurements to be made at the picomolar level—well within the range required and at least 10,000-fold more sensitive than reported elsewhere. Alternative methods of macromolecular analysis are largely qualitative and, therefore, inaccurate. The method of the present invention provides for highly accurate quantitative High sensitivity, and thus a high signal-to-noise ratio necessary to accurate quantitative analysis of low concentrations of interacting molecules, is achieved using an ILC 300 watt Xenon arc lamp/ISA monochromator excitation source coupled to the sample compartment through an Oriel rectangular to circular fused silica fiber optic cable. Film polarizers mounted on the sample holder in a crossed T-format in emission and with parallel orientation in excitation permit detection to the 10 picomolar limit. It is expected that since fluorescence is proportional to the excitation source intensity, the use of a laser excitation source will result in a 10 to 100-fold increase in sensitivity, well into the subpicomolar range of sample concentration.

Figure 5:
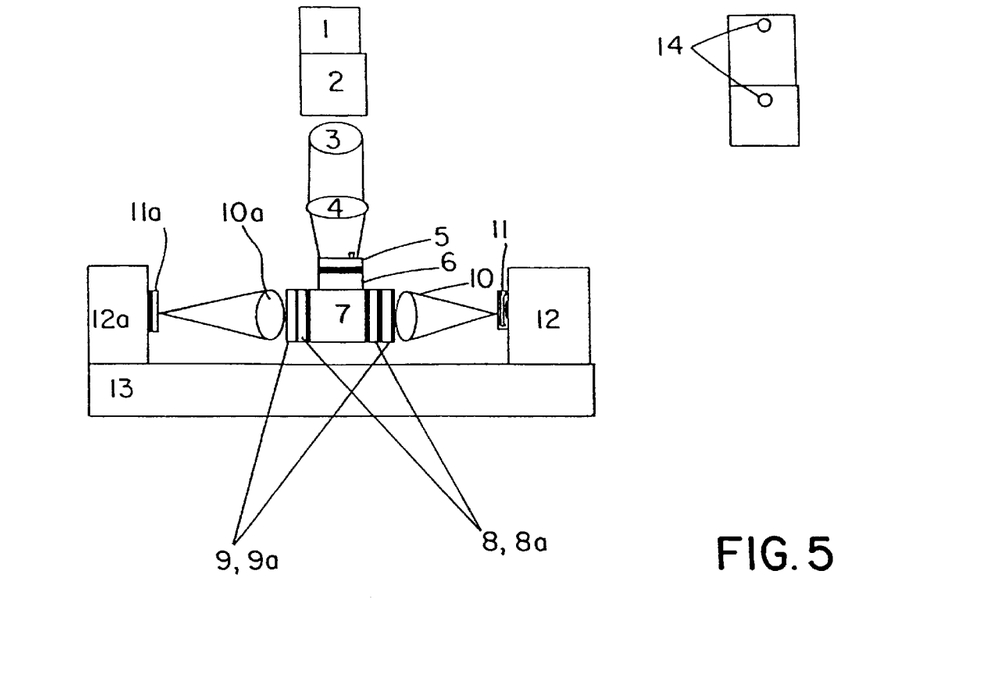
FIG. 5. Plan view drawing of a lamp-based, T-format high sensitivity polarization fluorometer.
Figure 6:
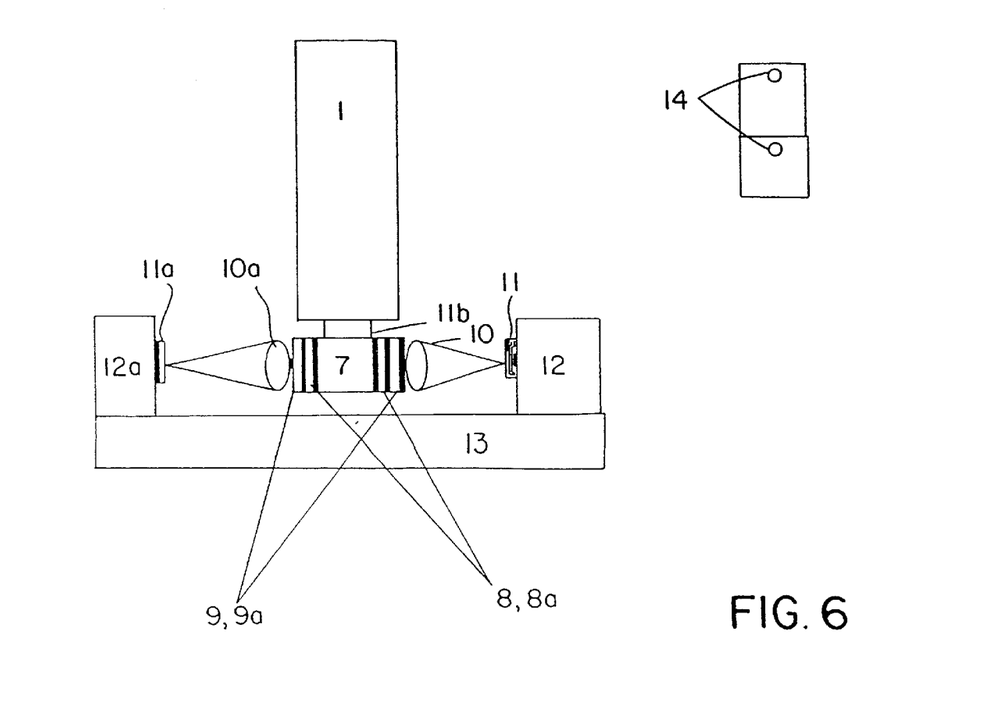
FIG. 6. Plan view drawing of a laser-based, T-format high sensitivity polarization fluorometer.

Several other embodiments of the apparatus can be used. The T-format using fixed polarizing elements as illustrated in FIGS. 5 and 6 can be changed to an L-format using a rotatable emission polarizer. Use of a laser illumination means eliminates the need for the excitation polarizer element (as laser light is plane polarized by its nature) and lenses for focusing the excitation light. Use of a laser tunable to several wavelengths, for instance a dye laser, provides for an apparatus having greater flexibility in the number of compounds which can be used as fluorescent labels in the assay of the present invention.

A preferred embodiment of the invention is an apparatus for measuring the polarization of fluorescent emission which can be understood by referring to the drawing FIGS. 5 and 6 and which comprises:

A box for the exclusion of light in which is placed an illumination means (1) so as to illuminate a sample chamber (7), through a collimating lens (3) and an excitation focusing lens (4) for collecting the light and focussing it upon the sample chamber, and further through a first polarizing means for plane polarizing the light from said illumination means (6), said lenses and first polarizing means, being mounted in a line connecting said illumination means and said sample chamber, and further said sample chamber being mounted between two additional polarizing means (8 and 8a), said polarizing means being placed so that the line between them and including said sample chamber is perpendicular to the light path from said illumination means to said sample chamber, said polarizing means being mounted so that the plane of polarization of the second of said polarizing means is parallel to the plane of polarization of said first polarizing means and also so that the plane of polarization of said second polarizing means is perpendicular to the plane of polarization of the third of said polarizing means and in which box is also placed detection means (12 and 12a) for the collection and quantitation of the amount of light which passes through said polarizing means from said sample chamber to said detecting means. Interposed between the emission polarizers and detection means are emission filters (9, 9a) for selectively passing light of a narrow range of wavelengths from the emission polarizers to the detecting means and also emission lenses (10, 10a) for focussing light emerging from the sample chamber onto the detecting means. Shutters (11, 11a) can also be interposed between the emission lenses and detection means for controlling the entry of light into the detection means and between the illumination means and the sample compartment (11b in FIG. 6) to control entry of light into the sample compartment. Enclosed in a separate compartment (13) are additional components of the apparatus including motors for driving the shutters and monochromator (if it is included) and electronic devices for data collection and processing.

Figure 7:
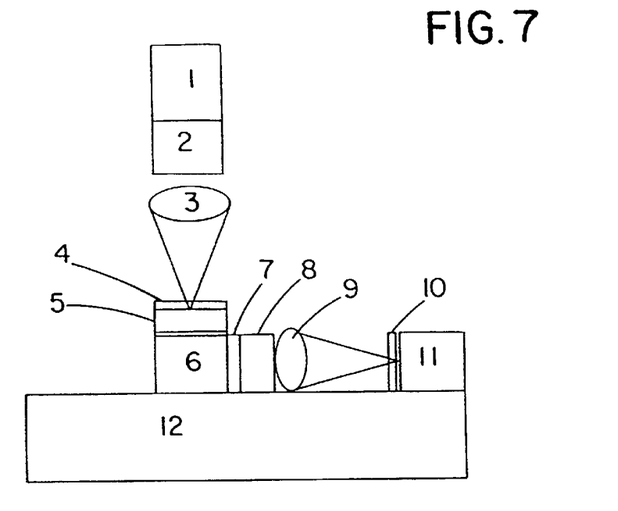
FIG. 7. Plan view drawing of a lamp-based, L-format high sensitivity polarization fluorometer.
Figure 8:
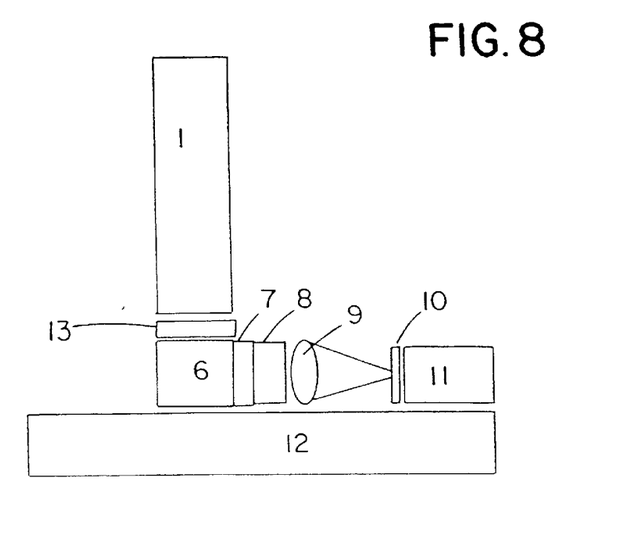
FIG. 8. Plan view drawing of a laser-based, L-format high sensitivity polarization fluorometer.
Figure 9:
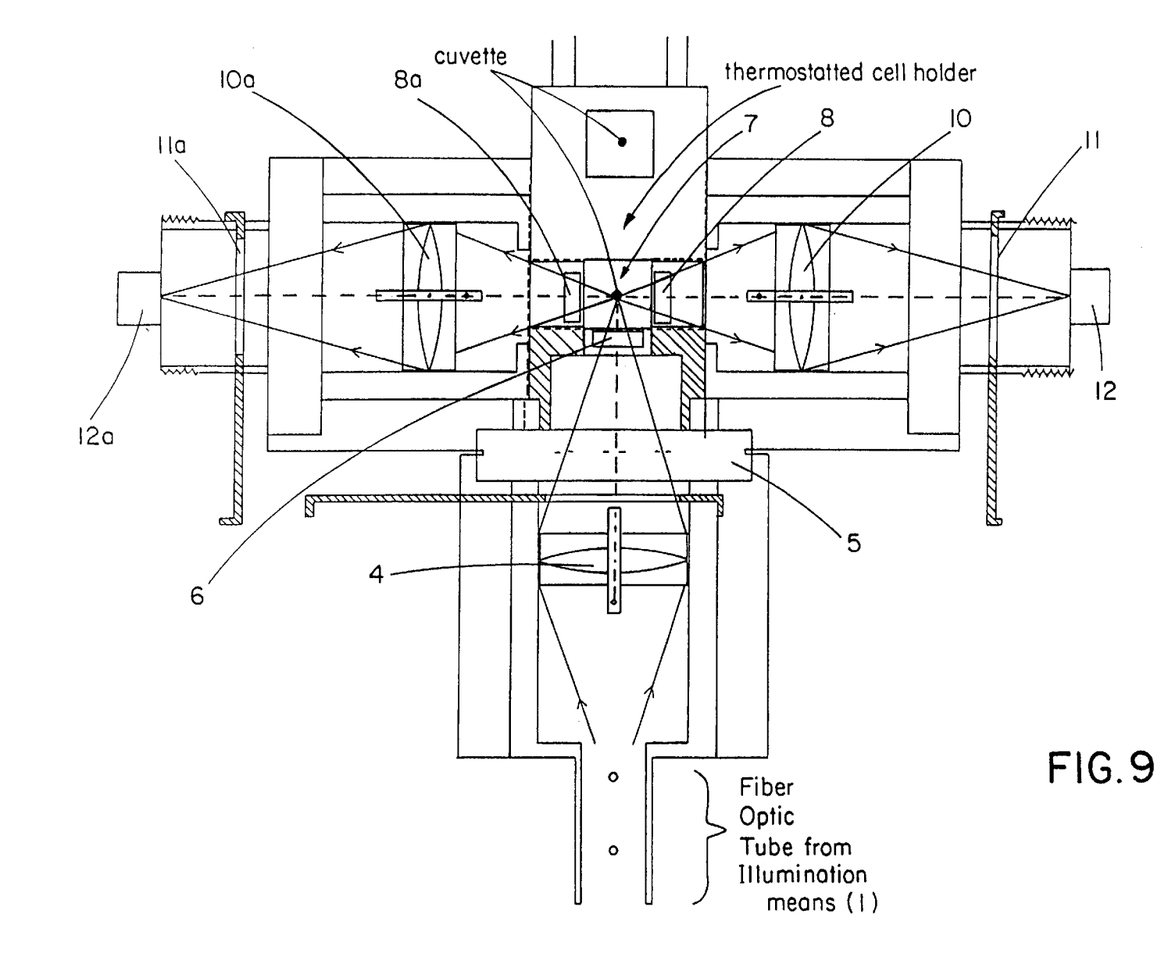
FIG. 9. Detail drawing in plan view of fiber optic, lamp-based, T-format high sensitivity polarization fluorometer, in particular showing detail of sample compartment and the arrangement of the film polarizers.

A second preferred embodiment of the invention is an apparatus for measuring the polarization of fluorescent emission which can be understood by referring to drawing FIGS. 7 and 8 and which comprises:

A box for the exclusion of light in which is placed an illumination means (1) so as to illuminate a sample chamber (6) through an excitation lens (3) for focussing the excitation light upon the sample chamber and further through an excitation filter (4), wherein said excitation filter passes only a narrow range of wavelengths of light, and finally through a fixed means of plane polarizing light which shines on said sample chamber (5), such that each of elements 3 and 4 and 5 are mounted in the light path from said illuminating means to said sample chamber, said sample chamber being mounted relative to a rotatable polarizing means (8), which plane polarizes light which passes through said rotatable plane polarizing means, so that a path from said illumination means through said sample chamber to said rotatable polarizing means forms a right angle with the sample chamber at the vertex and in which box is also placed an emission filter (7) interposed between the sample chamber and said rotatable plane polarizing means, wherein said emission filter will allow only a narrow range of wavelengths of light to pass and in which box is further mounted detection means (11) for the collection and quantitation of the amount of light which passes through said rotatable polarizing means from said sample chamber to said detecting means. Optionally interposed between the light source and the excitation lens is a monochromator (2) for selected particular wavelengths of light to be trained upon the sample chamber. Interposed between said emission polarizer and said detection means is an emission lens (9) for focussing the light emerging from said sample chamber upon said detection means and also an emission shutter (10) for controlling the entry of light into said detection means. Optionally interposed between said illumination means and said sample compartment is an excitation shutter (13 in FIG. 8) for controlling entry of light into the sample compartment. Other components of the machine are separately contained (12), including motors for rotating the emission polarizer, and electronic devices and motors for controlling the shutter and monochromator, and electronic devices for data processing.

It can be easily understood by reference to FIGS. 6 and 8 that when the light source is a laser, an excitation polarizer is not required, as laser light is intrinsically polarized. Similarly, tire nature of laser light makes the excitation collimating and focussing lenses unneccessary.

The fluorescent label can be covalently bound to a macromolecule by any of the many techniques commonly known in the art. Oligonucleotide probes can be labelled either along their backbone, at a position in the organic bases, or at either end. End-labelling of oligonucleotides with the fluorophore can be accomplished by chemically coupling an N-hydroxysuccinimide ester of the fluorophore to a 5'-amino group of the oligonucleotide which is produced during the synthesis of the oligonucleotide, or by using a phosphoramidite reagent derivatized with the fluorophore in the synthesis of the oligonucleotide. An oligonucleotide can also be labelled at the 3' end by tagging it with fluorescently labelled nucleotides using terminal transferase.

It is expected that the invention will be useful in the analysis of proteins, oligonucleotides, DNA, RNA and other macromolecules either biological or synthetic. Since the technique described in the present invention is performed in the solution phase, it is particularly useful in identifying those parameters of the solution which promote or interfere with complex formation between polynucleotides and other macromolecules, for instance, pH, salt concentration or the presence of co-factors. The sensitivity of the presently described technique is such that complex formation can be analyzed at concentrations of the macromolecules of less than 1 $\mu$M. The assay can easily be performed at macromolecule concentrations of 1 nM and can be done at concentrations ranging from 10 to 100 pM.

Oligonucleotides labeled with a wide range of fluorophores, including but not limited to fluorescein, eosin and coumarin may be used as probes. The identity of the fluorophore does not define the invention. The present invention encompasses any determination of the presence, character or amount of a macromolecule or any determination of specific intermolecular chemical parameters or constants in which measurement of the fluorescence polarization of a fluorescently labeled oligoniucleotide is employed.

The invention being thus described, preferred embodiments of the invention are set forth in the Examples below. These examples are meant only to be illustrative of the invention without being limiting of its scope.

EXAMPLE 1

Use of Fluorescence Anisotropy Measurements to Assay Protein-nucleic Acid Interactions Fluorescence polarization of a fluorescently modified oligonucleotide has been used to study the complex between an oligonucleotide and a protein. This was the case for the study of the interaction of Klenow fragment with a primer labeled with 5-dimethylamino-naphthalene-1-sulfonamide (12). However the goal of these studies was to gain specific structural information about the complex. Duo to the choice of the fluorophore and the instrumentation used in the study, the sensitivity of this assay was approximately 10 $\mu$M, 100,000 times less sensitive than the detection limit of the present invention. In fact, in those studies the authors were unable to quantitate reliably the strength of the interaction between the protein and the oligonucleotide because the concentrations required for detection were at least 10,000 times greater than the value of the dissociation constant between the species.

The polarization of fluorescence of 7-dimethylamino-3-(4'-maleimidylphenyl)-4-methylcoumarin covalently bound to a 32 base pair double-stranded oligodeoxynucleotide containing the lac promoter sequence was used to monitor the formation of a complex between the cAMP receptor protein and the lac promoter sequence (13). The concentration limit of the detection in this particular assay (10 nM) was several orders of magnitude above the interaction energy. It is also 1000-fold greater than the sensitivity of the assay described in this invention, which can detect analytes at picomolar concentrations.

The methodology of the present invention is based upon the observation of changes in the anisotropy or polarization of fluorescence of a fluorescent probe bound to a single or double-stranded oligonucleotide upon its interaction with a protein or other macromolecule. In the first set of experiments, monitoring protein-DNA interactions, the oligodeoxyribonucleotide was a 25 mer which was labeled on the 5'-end of the sense strand with fluorescein, using a fluorescein-labeled phosphoramidite reagent in automated DNA synthesis. The oligodeoxyribonucleotide was obtained commercially. The sequence of the sense strand was as follows (F=fluorescein):

5'-F-CTTGCACTAGTTAACTAGTCAGCAA-3'

The central CTAGAATTCTAG sequence is the specific operator binding site of the tryptophan repressor protein, which in the presence of its co-repressor tryptophan, binds with high affinity (0.5 nM as determined by gel retardation assays, Carey, 1988) to the target sequence. Thus, the protein used in these studies is the tryptophan repressor which was over-expressed and purified using the method of Paluh and Yanofsky (9), with modifications by Chou et al. (10).

The anti-sense strand of the double-stranded oligodeoxyribonucleotide was unlabeled. The two strands were annealed by dissolution in 500 mM KCl, 10 mM phosphate, 0.1 mM EDTA, ph 7.0 for final concentrations near 10–100 $\mu$M. Equimolar mixtures of the two strands as estimated from the optical density at 260 nm and the sequence of the strands Revere prepared and were heated to 85° C. for 10 minutes and allowed to cool slowly at room temperature.

The fluorescein-labeled double stranded oligodeoxyribonucleotide was diluted to its final concentration, usually 0.2 nM, in a total volume of 700 $\mu$l, directly into a reduced volume, 1.2 ml, fused silica cuvette. The assay buffer used for the dilution, 10 me potassium phosphate, 0.1 mM EDTA, pH 7.6 also contained 10% glycerol and in some cases 0.4 mM L-tryptophan. Upon dilution, the KCl concentration decreased to well below 1 mM. The solution was allowed to equilibrate 5 minutes before each polarization measurement.

The fluorescence polarization or anisotropy was measured in L-format using an ISS KOALA™ automated fluorometer or in T-format using our original sample holder and polarizer arrangement for the ultrahigh sensitivity determinations. The exciting light was set at 488 nm and emission was monitored through a Y520 long pass filter from Hoya optics. The background fluorescence from the buffer, which is non-negligible at concentrations below 10 nM was subtracted by sequential measurement of the parallel and perpendicular components of the sample and the buffer in a matched cuvette.

Sensitivity and Accuracy of the Measurements.

Figure 1A:
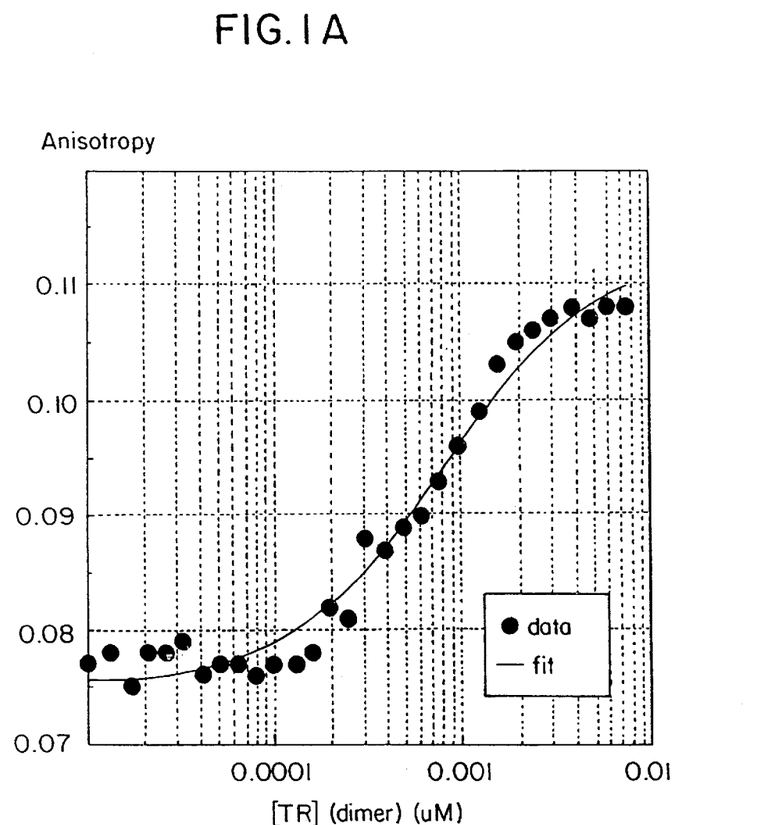
FIGS. 1A shows the titration of a fluorescein-labeled double-stranded oligodeoxynucleotide containing a trp operator sequence with purified tryptophan repressor protein. The buffer conditions were 10 mM phosphate, 0.1 mM EDTA, 10% glycerol, pH 7.6 in presence of 0.4 mM L-tryptophan. Total sample volume was 700 µl. The concentration of the fluorescein-labeled oligonucleotide was 200 pM. The anisotropy of fluorescence is plotted as a function of the logarithm of the protein concentration expressed as monomer. The lines through the points represent the non-linear analysis of the data in terms of a model in which a monomer/dimer equilibrium is coupled with the dimer-DNA binding equilibrium.
Figure 1B:
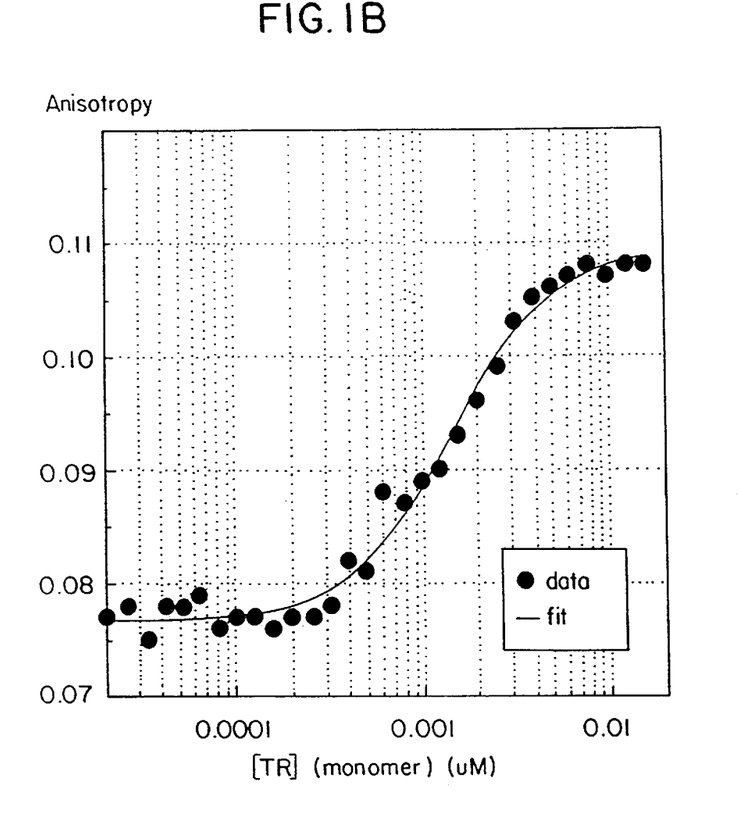
FIGS. 1C, 1D show the free energy diagrams for a simple binding scheme and the protein-protein and protein-DNA coupled interaction scheme. The data were fit using these two models, as shown in FIGS. 1A and 1B.

The assay was performed by sequential addition of the protein in extremely small aliquots (2 $\mu$l) in order that the total concentration of the oligodeoxyribonucleotide not decrease by more than 10%, upon the change in volume. The plots in FIGS. 1A and 1B show that upon sequential addition of the protein to the solution containing the fluorescein-labeled oligodeoxyribonucleotide and 0.4 mM L-tryptophan, the anisotropy of the fluorescence increases in a sigmoidal fashion, when plotted against the logarithm of the protein concentration expressed as dimer. Each measurement was repeated 4 times and the results were averaged. The error on each measurement was +/−0.002 polarization units. It can be seen that even when only 10% of the oligodeoxyribonucleotide, that is 20 pM, is bound by protein, the change in the anisotropy value is well beyond the error in the measurements.

We show in FIG. 1A that subnanomolar quantities of oligodeoxyribonucleotide can be detected and its binding to protein produces a signal change which is 15-fold greater than the error of the measurement.

EXAMPLE 2

Figure 1C:
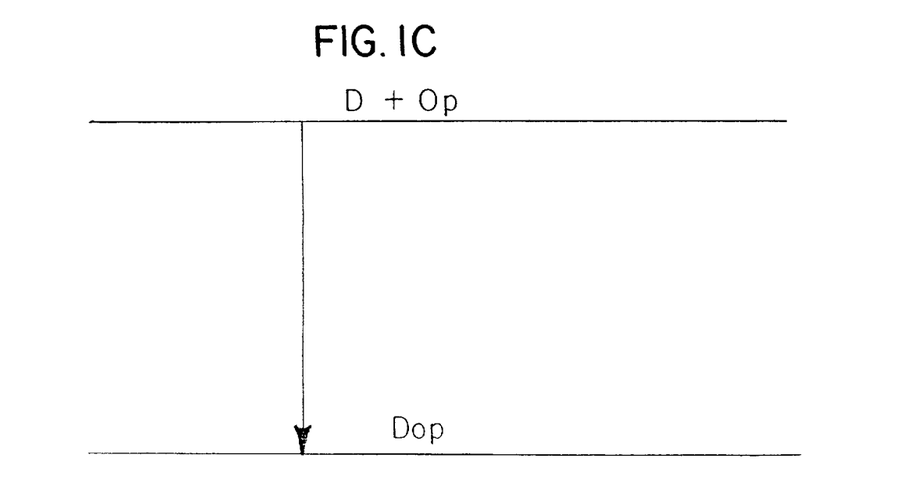
Figure 1D:
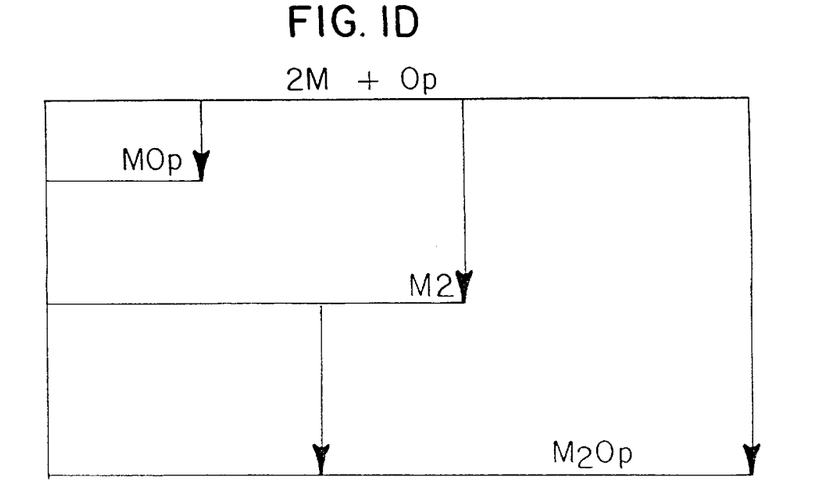
Figure 2:
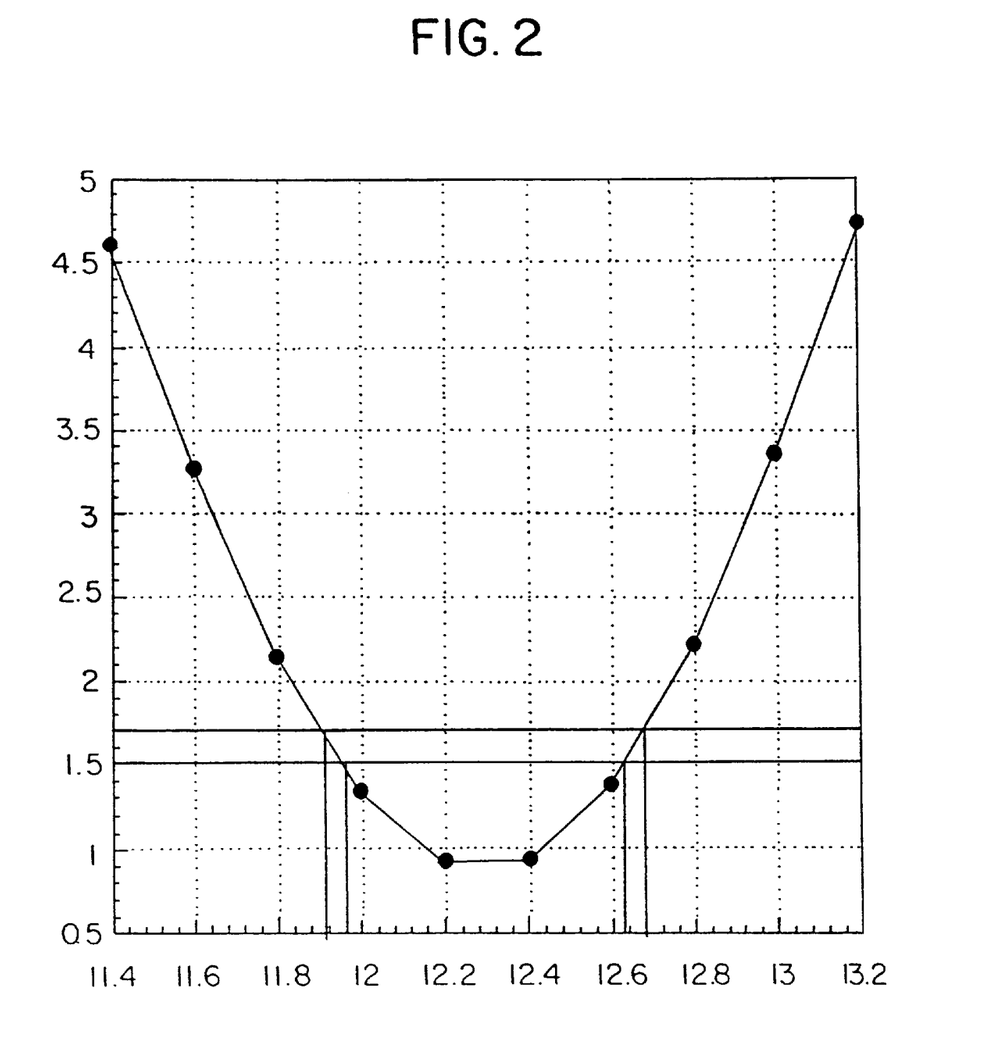
FIG. 2 Plot of $X^2$ (ordinate) vs. free energy in kcal (abscissa) for the thermodynamic model given in FIG. 1C

Use of Fluorescence Anisotropy Measurements to Evaluate Thermodynamic Models of Protein-nucleic Acid Interaction These data were analyzed in terms of two thermodynamic models, which are depicted in FIGS. 1C and 1D. The first (1C) is a simple protein-DNA binding model where the only species are the free protein, the free DNA and the protein-DNA complex. In the second model (FIG. 1D), a monomer-dimer equilibrium is superimposed upon the protein-DNA binding equilibrium. The fits of the data using these two models and the numerical equilibrium analysis program, BIOEQS, (20) are shown in FIGS. 1A and 1B. The dissociation constant for the tryptophan repressor dimer-DNA interaction as obtained using the simple binding model was found to be 0.83 nM. The fit of the data using the linked equilibria model yielded a dimer-DNA dissociation constant of 0.23 nM and a dimer-monomer dissociation constant of 3.5 nM. The quality of the data is sufficient to rule out the simple binding model; the fit is of much higher quality in the case of the linked equilibria (c.f., FIGS. 1A and 1B). Rigorous confidence level testing reveals a steep $X^2$ well for the dimer-DNA affinity, with 67% limits at +/−0.3 kcal (FIG. 2). Thus, not only can complex formation at low concentration be detected, but the quality of the data is sufficient that the affinity can be determined from the fit of the data, and the efficient evaluation of alternative thermodynamic models can be made.

EXAMPLE 3

Figure 3:
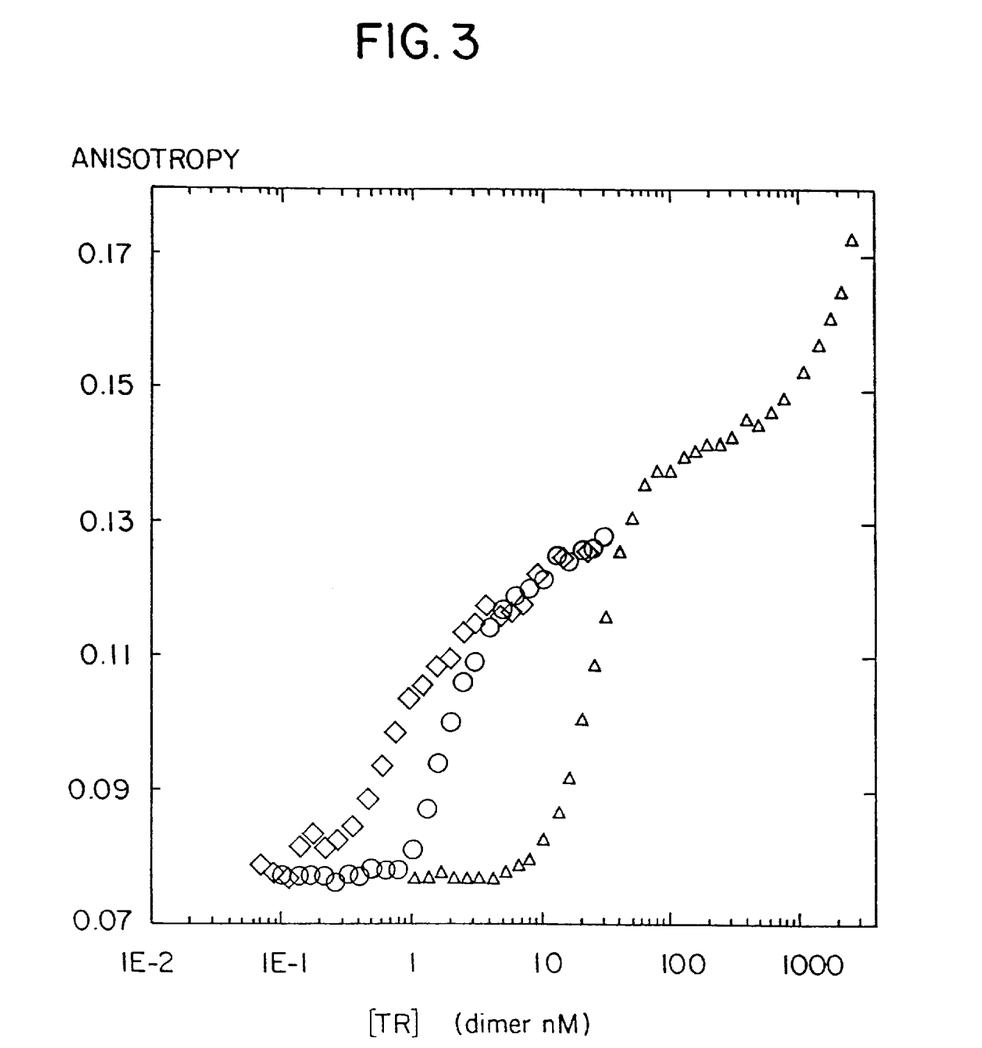
FIG. 3 shows the dependence of the binding profile of trp repressor to a synthetic oligonucleotide containing a trp operator sequence on the concentration of the oligonucleotide. The stoichiometry of the complexes formed is a subtle function of the absolute and relative concentrations of protein and oligonucleotide. Thus, a primary plateau is reached which is more apparent at low DNA concentrations, followed by a further increase in the anisotropy as higher order complexes are formed. DNA concentrations were 200 pM, 1 nM, and 20 nM.
Figure 4:
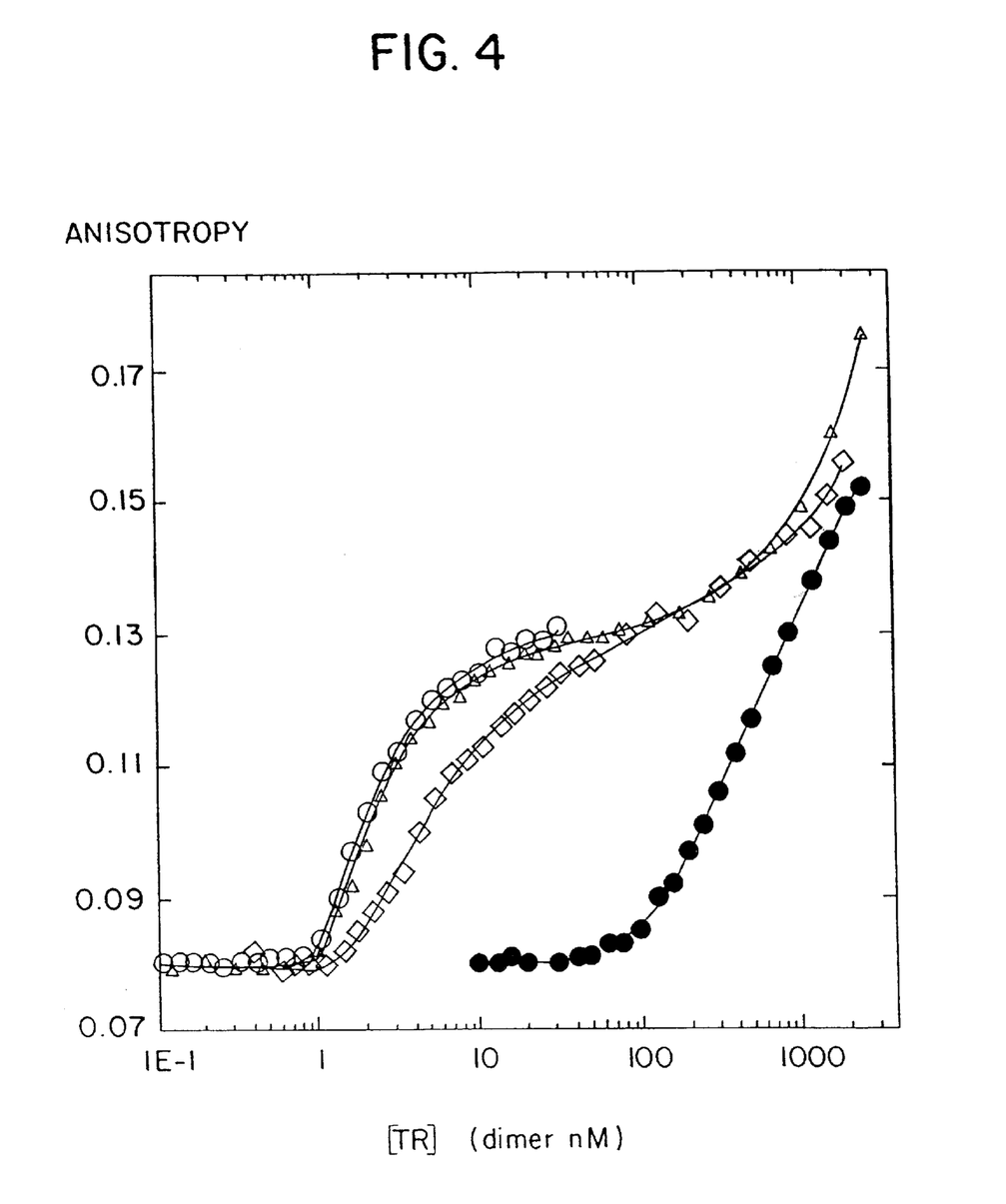
FIG. 4 shows the dependence of the binding of the trp repressor protein to the operator oligonucleotide upon the concentration of tryptophan. Open circles represent binding of protein to 1 nM oligonucleotide in presence of 4.0 mM tryptophan, open triangles show binding in the presence of 0.4 mM tryptophan, open diamonds 40 µM tryptophan and the closed circles denote the binding profile in absence of the tryptophan co-repressor.

Use of Fluorescence Anisotropy Measurements in the Analysis of Multi-component Systems in Solution The effect of changing the concentration of the DNA oligonucleotide and of titrating the protein to the concentrations found in vivo (near 1 μM) is shown in FIG. 3. It can be seen that complexes of higher molecular weight and thus higher anisotropy are favored at these higher concentrations of protein and DNA. Since this is a solution-based assay, the concentrations of any of the components can be varied easily. Thus, in FIG. 4, one can see the effect of omitting the L-tryptophan from the assay buffer. Using 20 nM oligodeoxyribonucleotide, binding is only observed at protein concentrations above approximately 1 μM in repressor protein dimer in the absence of tryptophan co-repressor.

We have thus demonstrated that these assays can be used to test quantitatively the effects of specific ligands or other drugs on formation of complexes between proteins and nucleic acids.

The results shown in FIGS. 1 to 4 clearly demonstrate that the polarization or anisotropy of fluorescence of fluorescently labeled oligodeoxyribonucleotides can be used to detect with high sensitivity and accuracy the interaction of the oligodeoxyribonucleotide with proteins and other large biological molecules. The fluorescence signal of fluorescein has been detected at concentrations as low as 10 pM in a total volume of 500 μl. One femtomole of a particular DNA binding protein is easily detected, using 10 femtomoles of the fluorescently labeled target sequence, given that binding of 10% of the oligonucleotide results in a signal change that can be measured accurately. High sensitivity and data quality provide a means for the detection of complex formation and also for the extremely accurate determination of the energetic strength of the interaction, as well as the discrimination between thermodynamic binding models. The assay is quite rapid, taking only 5–10 minutes per point. It is solution based, such that the effects of small ligands and drugs, pH, salt, temperature, and other solution conditions can be evaluated easily. For example, it would require approximately 10 minutes to ascertain whether crude cell extract or an in vitro translation assay contained a protein factor which had the ability to bind to a particular DNA sequence. A complete titration curve and its analysis requires approximately 45 minutes. Its ease of use, solution-based nature and rapidity make this assay a significant improvement over methods based on electrophoresis or filter-binding. This assay may be applied widely in the study of transcription factors and in the role of drugs and other small molecules in regulating genetic expression. Additional applications include clinically oriented tests for assaying function of transcription factors or other DNA binding proteins.

EXAMPLE 4

Use of Fluorescence Anisotropy Measurements to Assay Interactions Between Nucleic Acids The binding of a single-stranded oligonucleotide to another complementary single stranded DNA or RNA oligonucleotide can also be detected using this methodology. Demonstration of significant changes in anisotropy of fluorescence were made using the 5'-fluorescein labeled self-complementary 20 mer oligodeoxyribonucleotide,

5'-F-CGAACTAGTTAACTAGTACG-3'

(F indicates fluorescein). The change in anisotropy occurs upon conversion of the denatured single-stranded oligodeoxyribonucleotide to double-stranded form by the formation of a double-stranded complex with itself. Three tests were conducted. In each, two samples were compared. Each of the two samples contained labeled oligodeoxyribonucleotide in 500 μl of 10 mM $KPO_4$, 0.1 mM EDTA, pH 7.6 at a concentration of 50 nM. One of the two samples (high salt) contained in addition 1M KCl. The high salt sample was heated to 95° C. and cooled to room temperature. The heating and cooling at high salt results in conversion of largely single-stranded oligodeoxyribonucleotide into double-stranded form. This change in form should result in reduced Brownian motion with a consequent increase in anisotropy. Fluorescence anisotropy measurements were made on each pair of samples. The results of these measurements, given in Table I, demonstrate an increase in fluorescence anisotropy of at least 20-fold over the error in the measurement upon formation of the double-stranded complex.

TABLE I

DETECTION OF OLIGONUCLEOTIDE HYBRIDIZATION IN SOLUTION

| Test Number | Anisotropy Low salt, before heating | Anisotropy High salt, after heating |
|---|---|---|
| 1 | 0.046 +/− 0.001 | 0.067 +/− 0.000 |
| 2 | 0.042 +/− 0.001 | 0.065 +/− 0.000 |
| 3 | 0.044 +/− 0.001 | 0.066 +/− 0.001 |

The change would have been much larger if the oligonucleotide had been 8–10 bases long, or if the target sequence had been single-stranded plasmid DNA, as is also typically used in hybridization assays. Thus, the detection of the formation of the double-stranded 20 mer is well below the size differential typically involved when a small oligonucleotide binds to a large single-stranded DNA molecule.

The assay based on measurement of nucleic acid interactions has application in genetic mapping and in the clinical determination of the existence of specific mutations. It may also be used in the evaluation of translation inhibition by anti-sense DNA/RNA nucleic acids, a technique with potential applications in clinical diagnostics, therapeutics, or other biomedical areas. The fluorescence anisotropy measurements described herein are completely solution-based (i.e., require no solid support) a feature that will simplify automation of the assay. In conclusion, this invention represents a fast, accurate, reproducible, simple quantitative assay for the interactions of nucleic acids with other macromolecules.

EXAMPLE 6

Clinical Assay for Function of a DNA-binding Protein in a Tissue Biopsy

The method of the present invention is expected to find use in a clinical setting. Estrogen receptor is a DNA-binding protein, the dysfunction of which has been implicated in the etiology of breast cancer. Described herein is a method which could be employed to assay for functional estrogen receptor in biopsies from breast tissue.

A cell extract will be prepared from the biopsied tissue by gentle homogenization and centrifugation as described by Flanagan et al. (19). A double-stranded oligodeoxyribonucleotide which forms a consensus estrogen response element (ERE) can be prepared by automated synthesis of a pair of oligonucleotides. A preferred sequence for the sense strand is

5'-F-GGTCACTGTGACC-3' wherein the fluorophore (F) is incorporated by use of fluorescently-labelled phosphoramidite linker in the final nucleotide addition step of the synthesis. This oligonucleotide is self-complementary. Annealing of the oligonucleotide in solution provides a double-stranded oligonucleotide labelled with a fluorphore at each 5' end (*ERE).

The buffer for conducting the fluorescence polarization measurements is 10% glycerol, 80 mM KCl, pH 7.9 containing 0.2 mM EDTA. Measurements are made at room temperature.

Preliminary measurements are made of the fluorescence intensity of the cell extract containing no ERE oligonucleotide (background). These values are subtracted from the measurements used in determining the emission polarization of those samples which contain cell extract. Preliminary measurements are also made of the fluorescence polarization of the *ERE oligodeoxyribonucleotide in a solution free of the cell extract. Then aliquots of the cell extract are mixed with 1 pM of the *ERE oligodeoxyribonucleotide and the fluorescence polarization is again measured. Comparison of the polarization values obtained in the presence of cell extract with the value of the free *ERE provides a measure of the binding function of estrogen receptor present in the sample.

As a control experiment, results using a sample cell extract prepared from cells known to contain functional estrogen receptor should be obtained and compared with the results from the extract prepared from the clinical sample.

To most clearly describe the experiment, an example of sample formulations is provided in Table II.

TABLE II

SAMPLE FORMULATIONS FOR DETERMINING BINDING OF ERE TO ESTROGEN RECEPTOR IN A CLINICAL SAMPLE

|  | Biopsy | | | Background | | |
|---|---|---|---|---|---|---|
| [ERE] | *ERE | Extract | Buffer | *ERE | Extract | Buffer |
| 1 pM | 5[a] | 0 | 995 | 0 | 0 | 1000 |
| 1 pM | 5 | 100 | 895 | 0 | 100 | 900 |
| 1 pM | 5 | 250 | 745 | 0 | 250 | 750 |
| 1 pM | 5 | 500 | 455 | 0 | 500 | 500 |
| 1 pM | 5 | 950 | 45 | 0 | 950 | 50 |
|  | Control | | | Background | | |
| [ERE] | *ERE | Extract | Buffer | *ERE | Extract | Buffer |
| 1 pM | 5 | 0 | 995 | 0 | 0 | 1000 |
| 1 pM | 5 | 100 | 895 | 0 | 100 | 900 |
| 1 pM | 5 | 250 | 745 | 0 | 250 | 750 |
| 1 pM | 5 | 500 | 455 | 0 | 500 | 500 |
| 1 pM | 5 | 950 | 45 | 0 | 950 | 50 |

[a]All amounts are in $\mu$l.

To quantitate the amount of estrogen receptor in the sample, the cell extract can be titrated with various amounts of labelled *ERE and the result compared with a standard curves obtained using known amounts of purified estrogen receptor and *ERE.

EXAMPLE 7

Clinical-Assay for a Specific Point Mutation in a Gene by Oligonucleotide Hybridization to mRNA from a Tissue Biopsy Specific mutations in the cholesterol receptor gene have been found to lead to hypercholesterolemia, a condition which leads to early death of the patient due to arterial disease if measures are not taken to control cholesterol levels in the circulation. It is expected that early detection of the condition by neonatal or prenatal genetic testing, and thus early intervention would provide for a better prognosis for afflicted individuals. Accordingly, in this example, a method for detecting mutations in the cholesterol receptor gene by assay of mRNA for binding to oligonucleotide probes is described. This method is of course generalizable to the detection of other mutations.

8–10 base oligonucleotides, labelled on the 5' end by methods known in the art, are designed to be complementary to those portions of the mRNA transcript of the wild type cholesterol receptor gene which have been previously shown to be mutated in patients having familial hypercholesterolemia. Each oligonucleotide is designed to provide a similar decrease in $T_m$ (the melting temperature of a duplex between the oligo and a hybridized complementary strand) upon binding to a sequence that is entirely complementary, with the exception of a single mismatched base pair, by varying its length and GC-content. An experiment is conducted to determine the temperature at which the wild type mRNA remains mostly hybridized to each oligonucleotide, but mRNA obtained from a liver biopsy of a panel of patients which present the mutations observed to cause hypercholesterolemia is not hybridized by the oligonucleotide complementary to the wild type sequence in the mutated region.

100 mg of tissue generally yields approximately 1 pmole of a specific 1 kilobase mRNA. In a volume of 1 ml, this would correspond to 1 nM of specific mRNA. For a 1:1 hybridization, 1 nM fluorescently labelled oligonucleotide would be used. This sample size provides a readily detected signal; thus smaller samples could be used. The fluorescence polarization of the oligonucleotide alone, mixed with wild-type mRNA at 1 nM and mixed with mRNA from the clinical sample at approximately 1 nM are each determined at the temperature found in the initial experiment to provide the maximal difference in binding of the oligonucleotide to the wild-type and the mutant mRNA sequence. It would be observed that tissue containing the wild-type mRNA would show a polarization greater than that observed for the oligonucleotide alone, while tissue containing mutant mRNA would show a polarization equal to that of the oligonucleotide alone.

As a control experiment, the fluorescence emission of the mRNA preparation in the absence of labelled oligonucleotide is determined in each plane of emission polarization. These background values are subtracted from each measurement made in the hybridization experiments.

EXAMPLE 8

Apparatus for Conducting Fluorescence Polarization Measurements with High Sensitivity The diagram shown in FIG. 5 shows modifications made to an ISS Koala™ fluorometer to produce an instrument having the sensitivity required to implement the present invention. The modifications include (1) reducing the light path from 30 cm to 20 cm; (2) positioning the emission lens to within 1 cm of the sample holder; and (3) replacing the Glan Thompson polarizers with UV grade film polarizers mounted directly on the sample holder. These improvements increase the instrument sensitivity dramatically. In the tests done to demonstrate the increase in sensitivity achieved by these modifications, a fluorescently labeled 25 mer oligonucleotide with the following sequence was used.

5'-F-ATCGAACTAGTTAACTAGTACGCAA-3'

As shown in Table III, we were able to detect oligonucleotide at a concentration of 9 pM in 500 $\mu$l using a Xenon arc lamp excitation source rather than the argon ion source indicated in the drawing. This represents an increase in sensitivity of 10-fold as compared to the unmodified instrument. Given that we can detect a 10% change in the polarization, we can therefore detect 0.9 pM of protein or nucleic acid or synthetic polymer in solution. This level of sensitivity corresponds to 450 attomoles of macromolecule

TABLE III

SENSITIVITY LIMIT ASSAY
USING MODIFIED FLUOROMETER AND SAMPLE CELL

| Solution | Intensity (Counts) |
|---|---|
| 9 pM F-25 mer | 1967.8 +/- 1.2 |
| Buffer background | 243.9 +/- 0.4 |

Sensitivity of the modified instrument could be improved by two further modifications. (1) Including a sharp bandpass excitation filter would increase sensitivity by a factor of 10-fold. (2) Substitution of an argon ion laser light source for the Xenon arc lamp used in the test reported herein would increase sensitivity by an additional 100-fold due to the increased intensity of the excitation beam and its monochromatic and polarized nature. Since we are background limited and the monochromators in the basic ISS instrument are not good at stray light rejection, most of the background intensity results from scattered exciting light. With a laser, there is only 488 nm light, and thus no stray light of other wavelengths will enter the sample. Secondly, laser light is plane polarized, eliminating the need for an excitation polarizer. Finally, fluorescence intensity is directly proportional to the excitation source intensity, and a laser, even a small one, would provide more power than the Xenon arc lamp. In the modified design, dilution with concomitant increase in gain did not increase sensitivity, since use of a lamp excitation source caused the detection level to be background-limited rather than noise-limited. Thus, another factor of 10 increase in sensitivity is available if the stray exciting light can be eliminated.

The invention being thus described, various modifications of the materials and methods set forth in the description will be obvious to a practitioner of the invention who is skilled in the art. Such variations upon the invention described are to be considered within the scope of the invention as claimed below.

REFERENCES

The following references are cited in the disclosure. Each of the references below is hereby incorporated in its entirety by such citation.

| 1. 4,269,511 | 5/1981 | to | Erwin |
| 2. 4,516,856 | 5/1985 | to | Popelka |
| 3. 4,585,862 | 4/1986 | to | Wang, C-H, et al. |
| 4. 4,668,640 | 5/1987 | to | Wang, C-H, et al. |
| 5. 4,784,961 | 11/1988 | to | Russell |
| 6. 4,902,630 | 2/1990 | to | Bennet, L.G. and Chiapetta, G. |
| 7. 4,952,691 | 8/1990 | to | Wang et al. |
| 8. 5,066,426 | 11/1991 | to | Wang, et al. |

OTHER REFERENCES

9, Paluh, J. L. and Yanofsky, C. (1983) Nucl. Acids Res. 14, 7851–60

10 Chou, W-Y., Buber, C., and Matthews K. S. (1989) J. Biol Chem. 264 18309–13

11, Carey, J., (1988) Proc. Natl. Acad. Sci 85, 975–9

12, Guest, C. R., Hochstrasser, R. A., Dupuy, C. G., Allen, D. J., Benkovic, S. J., and Miller D. P. (1991) Biochemistry 30, 8759–70.

13, Heyduk, T. and Lee, J. C. (1990) Proc. Natl. Acad. Sci. 87 1744–8

14, Beecham, J. M., (1992) Methods in Enzymology Vol 210, pg. 37–53.

15, Urios, P and Cittanova, N. (1990) Anal. Bioc. 185 308–12

16, Giedroc, D. P., Khan, R., and Barnhart, K. (1991) Biochem. 30 8230–42

17, Murakami, A., Nakaura, M., Nakatsuji, Y., Nagahara, S., Tran-Cong, Q., and 18, Makino, K. (1991) Nucl. Acids Res. 19 4907–4912.

19, P. M. Flanagan et al. (1992) Proc. Natl. Acad. Sci. USA 89:7659–7663.

20, C. A. Royer et al. (1990) Anal. Biochem. 191:287–294

What is claimed is:

1. A method for measuring the binding of a polynucleotide to a protein to form a complex which comprises:

i) labeling said polynucleotide with a fluorescent label;

ii) obtaining a first measurement of the polarization of the fluorescent emission from said label;

iii) contacting said labeled polynucleotide with said protein, such that the concentration of said labeled polynucleotide is in the range of 10 picomolar to 10 nanomolar;

iv) obtaining a second measurement of the polarization of the fluorescent emission from said label;

v) comparing said first measurement with said second measurement; and vi) detecting formation of said complex by observing an increase in the polarization measured in step (iv) compared to the polarization measured in step (ii);

wherein said polarization measurements are made using an apparatus comprising at least one film polarizer.

2. A method as recited in claim 1, wherein said label is fluorescein.

3. A method as recited in claim 1, wherein said polynucleotide is a single-stranded oligodeoxyribonucleotide of length less than or equal to 40 bases.

4. A method as recited in claim 1, wherein said polynucleotide is a double-stranded oligodeoxyribonucleotide of length less than or equal to 40 basepairs.

5. A method as recited in claim 1, wherein said polynucleotide is present at a concentration of less than or equal to 1 nanomolar.

6. The method as recited in claim 5, wherein said protein is present at a concentration of less than or equal to 1 nanomolar.

7. A method for diagnosing variation in the amount or nature of a DNA binding protein which comprises:

i) fluorescently labelling an oligonucleotide having the nucleotide sequence recognized by a DNA-binding protein, wherein said oligonucleotide may be either double-stranded or single stranded.

ii) obtaining a sample containing the DNA-binding protein to be tested;

iii) obtaining a first measurement of the-polarization of the fluorescent emission from said fluorescently-labelled oligonucleotide;

iv) contacting said fluorescently-labelled oligonucleotide with said sample under conditions favorable to binding of said fluorescently-labelled polynucleotide to said DNA-binding protein;

v) obtaining a second measurement of the polarization of the fluorescent emission from said fluorescently-labelled oligonucleotide under said conditions favorable to binding; and vi) comparing said second measurement to said first measurement.

8. The method of claim 6, which further comprises:

vii) adding a second aliquot of unlabelled polynucleotide having the same nucleotide sequence as said labelled polynucleotide;

viii) obtaining a third measurement of the polarization of the fluorescent emission from said fluorescently-labelled oligonucleotide under said conditions favorable to binding; and vi) comparing said measurement to said first and second measurements.

* * * * *